US010975429B2

(12) United States Patent
Drews et al.

(10) Patent No.: US 10,975,429 B2
(45) Date of Patent: Apr. 13, 2021

(54) SYSTEM AND METHODS FOR SELECTIVE EFFLUENT COLLECTION

(71) Applicant: Illumina, Inc., San Diego, CA (US)

(72) Inventors: Bradley Kent Drews, Poway, CA (US); Kevin James Cappa, San Diego, CA (US); Matthew William Hage, San Diego, CA (US)

(73) Assignee: ILLUMINA, INC., San Diego, CA (US)

(*) Notice: Subject to any disclaimer, the term of this patent is extended or adjusted under 35 U.S.C. 154(b) by 276 days.

(21) Appl. No.: 15/841,082

(22) Filed: Dec. 13, 2017

(65) Prior Publication Data
US 2018/0187259 A1 Jul. 5, 2018

Related U.S. Application Data

(60) Provisional application No. 62/442,742, filed on Jan. 5, 2017.

(30) Foreign Application Priority Data

Mar. 24, 2017 (GB) .................................. 1704766.3

(51) Int. Cl.
*C12Q 1/6874* (2018.01)
*B01L 3/00* (2006.01)
*C12Q 1/6869* (2018.01)

(52) U.S. Cl.
CPC ............ *C12Q 1/6874* (2013.01); *B01L 3/502* (2013.01); *C12Q 1/6869* (2013.01);
(Continued)

(58) Field of Classification Search
CPC ................ C12Q 1/6874; C12Q 1/6869; C12Q 2563/107; C12Q 2565/601;
(Continued)

(56) References Cited

U.S. PATENT DOCUMENTS

2004/0072278 A1* 4/2004 Chou ................ B01L 3/502761
435/29
2004/0181343 A1* 9/2004 Wigstrom ............. B01L 3/5027
702/19

(Continued)

FOREIGN PATENT DOCUMENTS

EP 1437597 7/2004
WO 2018/128844 7/2018

OTHER PUBLICATIONS

PCT/US2017/067841, International Search Report and Written Opinion dated Apr. 23, 2018, 18 pages.

(Continued)

*Primary Examiner* — Benjamin R Whatley
*Assistant Examiner* — Quocan B Vo
(74) *Attorney, Agent, or Firm* — Illumina, Inc.

(57) ABSTRACT

A system may include a flow cell through which a plurality of reagents may be pumped during a genetic sequencing operation, an effluent line that, in operation, is to conduct a used reagent, a used reagent valve to receive the used reagent from the effluent line and controllable to select one of a plurality of disposal paths for the used reagent, and control circuitry coupled to the used reagent valve that, in operation, is to control the used reagent valve to select a desired one of the disposal paths depending upon which reagent is being pumped though the flow cell.

19 Claims, 5 Drawing Sheets

(52) U.S. Cl.
CPC . *B01L 2200/0605* (2013.01); *B01L 2200/143* (2013.01); *B01L 2200/16* (2013.01); *B01L 2300/0861* (2013.01); *B01L 2300/0877* (2013.01); *B01L 2400/06* (2013.01)

(58) Field of Classification Search
CPC .............. C12Q 2565/629; B01L 3/502; B01L 2200/0605; B01L 2400/06; B01L 2300/0877; B01L 2200/143; B01L 2300/0861; B01L 2200/16
See application file for complete search history.

(56) References Cited

U.S. PATENT DOCUMENTS

| | | |
|---|---|---|
| 2010/0111768 A1 | 5/2010 | Banerjee et al. |
| 2010/0300895 A1 | 12/2010 | Nobile et al. |
| 2013/0260372 A1 | 10/2013 | Buermann et al. |
| 2014/0177378 A1* | 6/2014 | Kahlon ............... G05D 11/138 366/132 |
| 2015/0346149 A1 | 12/2015 | Brown et al. |
| 2015/0361488 A1 | 12/2015 | Schultz et al. |
| 2016/0047805 A1 | 2/2016 | Quinn |
| 2016/0319350 A1 | 11/2016 | Stone et al. |

OTHER PUBLICATIONS

GB Search Report, dated Oct. 2, 2017, in Application No. GB1704766.3.

* cited by examiner

SYSTEM AND METHODS FOR SELECTIVE EFFLUENT COLLECTION

CROSS-REFERENCE TO RELATED APPLICATIONS

This application claims benefit of priority to British (GB) Patent Application No. 1704766.3, filed Mar. 24, 2017, which claims benefit of priority to U.S. Patent Application No. 62/442,742, filed Jan. 5, 2017, as well as benefit of priority under 35 U.S.C. § 119(e) to U.S. Patent Application No. 62/442,742, filed Jan. 5, 2017, both of which are hereby incorporated by reference herein in their entireties.

BACKGROUND

Instruments have been developed and continue to evolve for sequencing molecules of interest, particularly DNA, RNA and other biological samples. In advance of sequencing operations, samples of the molecules of interest are prepared in order to form a library or template which will be mixed with reagents and ultimately introduced into a flow cell where individual molecules will attach at sites and be amplified to enhance detectability. The sequencing operation, then, includes repeating a cycle of steps to bind the molecules at the sites, tag the bound components, image the components at the sites, and process the resulting image data.

In such sequencing systems, fluidic systems (or subsystems) provide the flow of substances (e.g., the reagents) under the control of a control system, such as a programmed computer and appropriate interfaces.

SUMMARY

Details of one or more implementations of the subject matter described in this specification are set forth in the accompanying drawings and the description below. Other features, aspects, and advantages will become apparent from the description, the drawings, and the claims.

In some implementations, a system may be provided that includes: one or more effluent flow paths to fluidically connect with a flow cell through which a plurality of reagents is to be pumped during a genetic sequencing operation, in which the effluent paths are to receive used reagents from the flow cell; one or more pumps to pump the used reagents through the effluent flow paths; a used reagent selector valve to receive used reagents from the one or more pumps via an effluent line and controllable to select one of a plurality of disposal paths for the used reagents; and control circuitry operatively coupled to the used reagent selector valve, the control circuity having one or more processors and a memory to store, or storing, machine-executable instructions which, when executed by the one or more processors, control the one or more processors to cause the used reagent selector valve to select a desired one of the disposal paths depending upon which used reagent is being pumped through the effluent paths.

In some implementations of the system, the system may further include a flow meter that, in operation, is to detect flow of used reagents and provide flow data regarding the flow of the used reagents to the control circuitry.

In some such implementations of the system, the flow meter may be fluidically coupled to one of the disposal paths, and the memory may be to store, or may store, further machine-executable instructions which, when executed by the one or more processors, further control the one or more processors to determine whether the used reagent is flowing through the desired flow path based upon feedback from the flow meter.

In some implementations of the system, a first disposal path of the disposal paths may convey more used reagent than a second disposal path of the disposal paths during the sequencing operation and the flow meter may be coupled to the first disposal path.

In some implementations of the system, the memory may be to store, or may store, further machine-executable instructions which, when executed by the one or more processors, further control the one or more processors to control the used reagent selector valve based upon a prescribed sequencing protocol for a genetic sequencer.

In some implementations of the system, the system may further include at least one valve to select a reagent and a reagent flow path, and the memory may be to store, or may store, further machine-executable instructions which, when executed by the one or more processors, further control the one or more processors to control the at least one valve and the used reagent selector valve based upon the prescribed sequencing protocol.

In some implementations of the system, the system may further include a reagent pump fluidically interposed between the reagent flow path and the effluent line.

In some implementations of the system, the system may further include a first used reagent vessel to receive used reagent from a first disposal path of the disposal paths and a second reagent vessel to receive used reagent from a second disposal path of the disposal paths.

In some implementations of the system, the first used reagent vessel may direct fluid therein to be directed away from an opening of the first used reagent vessel when the fluid is moved during removal or transport of the first used reagent vessel.

In some implementations, a system may be provided that includes: a flow cell through which a plurality of reagents is pumped during a genetic sequencing operation to produce used reagents; at least one reagent selector valve to select a reagent and a reagent flow path from a plurality of reagent flow paths, at least one of the reagent flow paths passing through the flow cell; an effluent line that, in operation, is to conduct used reagent; a used reagent selector valve to receive used reagent from the effluent line and controllable to select one of a plurality of disposal paths for the used reagent; and control circuitry operatively coupled to the at least one reagent selector valve and to the used reagent selector valve, the control circuity having one or more processors and a memory to store machine-executable instructions which, when executed by the one or more processors, control the one or more processors to control the at least one reagent selector valve and the used reagent selector valve based upon a prescribed sequencing protocol for the genetic sequencing operation.

In some implementations of the system, the memory may be to store, or may store, further machine-executable instructions which, when executed by the one or more processors, further control the one or more processors to select a desired one of the disposal paths depending upon which reagent is being pumped though the flow cell.

In some implementations of the system, the system may further include a flow meter that, in operation, is to detect flow of the reagents and provide flow data to the control circuitry.

In some such implementations of the system, the flow meter may be coupled to one of the disposal paths, and the memory may be to store, or may store, further machine-executable instructions which, when executed by the one or more processors, further control the one or more processors to determine whether the reagents are flowing through the desired flow path based upon feedback from the flow meter.

In some implementations of the system, a first disposal path of the disposal paths may convey more used reagent than a second disposal path of the disposal paths during the sequencing operation, and the flow meter may be fluidically coupled to the first disposal path.

In some implementations, a method may be provided that includes: performing a genetic sequencing operation by pumping a plurality of reagents through a flow cell to produce used reagents; during the genetic sequencing operation, controlling at least one reagent selector valve to select desired reagents to be pumped thought the flow cell in accordance with a protocol for the genetic sequencing operation; and during the genetic sequencing operation, controlling a used reagent selector valve to select one of a plurality of disposal paths for the used reagents after the used reagents exit the flow cell, the controlling of the used reagent selector valve using the protocol for the genetic sequencing operation.

In some implementations of the method, the method may further include detecting flow through at least one of the disposal paths to verify that used reagents are flowing through the selected disposal path.

In some implementations of the method, the flow may be detected by a flow meter fluidically coupled to one of the disposal paths.

In some implementations of the method, a first disposal path of the disposal paths may convey more used reagent than a second disposal path of the disposal paths during the sequencing operation, and the flow meter may be fluidically coupled to the first disposal path.

In some implementations of the method, the method may further include collecting the used reagents in at least two different vessels, each disposal vessel positioned to receive used reagents from a different disposal path.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
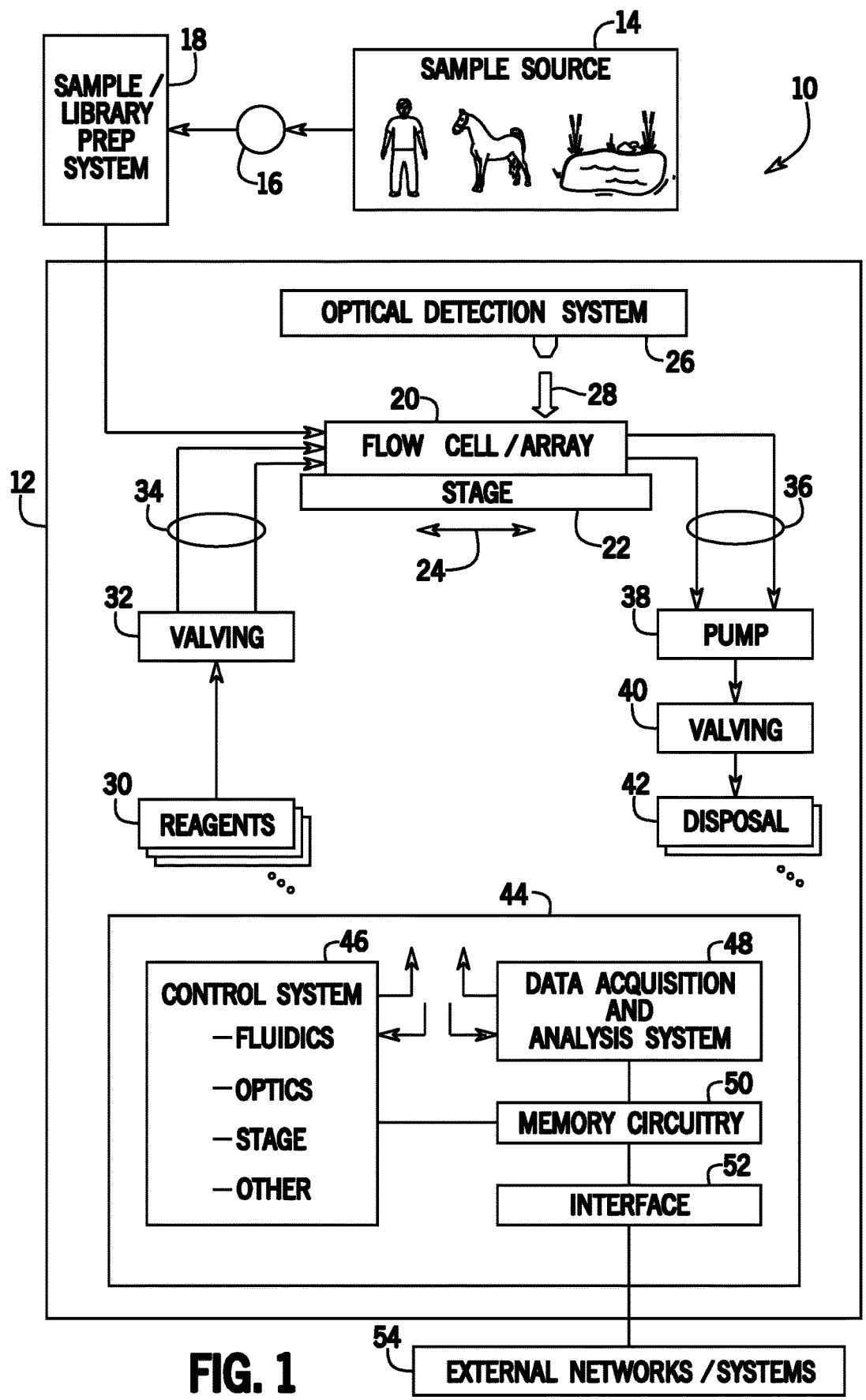
FIG. 1 is a diagrammatical overview of an example sequencing system in which the disclosed techniques may be employed.

FIG. 1 illustrates an implementation of a sequencing system 10 configured to process molecular samples that may be sequenced to determine their components, the component ordering, and generally the structure of the sample. The system includes an instrument 12 that receives and processes a biological sample. A sample source 14 provides the sample 16, which in many cases will include a tissue sample. The sample source may include, for example, an individual or subject, such as a human, animal, microorganism, plant, or other donor (including environmental samples), or any other subject that includes organic molecules of interest, the sequence of which is to be determined. The system may be used with samples other than those taken from organisms, including synthesized molecules. In many cases, the molecules will include DNA, RNA, or other molecules having base pairs the sequence of which may define genes and variants having particular functions of ultimate interest.

The sample 16 is introduced into a sample/library preparation system 18. This system may isolate, break, and otherwise prepare the sample for analysis. The resulting library includes the molecules of interest in lengths that facilitate the sequencing operation. The resulting library is then provided to the instrument 12 where the sequencing operation is performed.

In the implementation illustrated in FIG. 1, the instrument includes a flow cell or array 20 that receives the sample library. The flow cell includes one or more fluidic channels that allow for sequencing chemistry to occur, including attachment of the molecules of the library, and amplification at locations or sites that can be detected during the sequencing operation. For example, the flow cell/array 20 may include sequencing templates immobilized on one or more surfaces at the locations or sites. A "flow cell" may include a patterned array, such as a microarray, a nanoarray, and so forth. In practice, the locations or sites may be disposed in a regular, repeating pattern, a complex non-repeating pattern, or in a random arrangement on one or more surfaces of a support. To enable the sequencing chemistry to occur, the flow cell also allows for introduction of substances, such as including various reagents, buffers, and other reaction media, that are used for reactions, flushing, and so forth. The substances flow through the flow cell and may contact the molecules of interest at the individual sites.

In the instrument 12, the flow cell 20 is mounted on a movable stage 22 that, in this implementation, may be moved in one or more directions as indicated by reference numeral 24. The flow cell 20 may, for example, be provided in the form of a removable and replaceable cartridge that may interface with ports on the movable stage 22 or other components of the system in order to allow reagents and other fluids to be delivered to or from the flow cell 20. The stage is associated with an optical detection system 26 that can direct radiation or light 28 to the flow cell during sequencing. The optical detection system may employ various methods, such as fluorescence microscopy methods, for detection of the analytes disposed at the sites of the flow cell. By way of a non-limiting example, the optical detection system 26 may employ confocal line scanning to produce progressive pixilated image data that can be analyzed to locate individual sites in the flow cell and to determine the type of nucleotide that was most recently attached or bound to each site. Other suitable imaging techniques may also be employed, such as techniques in which one or more points of radiation are scanned along the sample or techniques employing "step and shoot" imaging approaches. The optical detection system 26 and the stage 22 may cooperate to maintain the flow cell and detection system in a static relationship while obtaining an area image, or, as noted, the flow cell may be scanned in any suitable mode (e.g., point scanning, line scanning, "step-and-shoot" scanning).

While many different technologies may be used for imaging, or more generally for detecting the molecules at the sites, presently contemplated implementations may make use of confocal optical imaging at wavelengths that cause excitation of fluorescent tags. The tags, excited by virtue of their absorption spectrum, return fluorescent signals by virtue of their emission spectrum. The optical detection system 26 is configured to capture such signals, to process pixelated image data at a resolution that allows for analysis of the signal-emitting sites, and to process and store the resulting image data (or data derived from it).

In a sequencing operation, cyclic operations or processes are implemented in an automated or semi-automated fashion in which reactions are promoted, such as with single nucleotides or with oligonucleotides, followed by flushing, imaging and de-blocking in preparation for a subsequent cycle. The sample library, prepared for sequencing and immobilized on the flow cell, may undergo a number of such cycles before all useful information is extracted from the library. The optical detection system may generate image data from scans of the flow cell (and its sites) during each cycle of the sequencing operation by use of electronic detection circuits (e.g., cameras or imaging electronic circuits or chips). The resulting image data may then be analyzed to locate individual sites in the image data, and to analyze and characterize the molecules present at the sites, such as by reference to a specific color or wavelength of light (a characteristic emission spectrum of a particular fluorescent tag) that is detected at a specific location, as indicated by a group or cluster of pixels in the image data at the location. In a DNA or RNA sequencing application, for example, the four common nucleotides may be represented by distinguishable fluorescence emission spectra (wavelengths or wavelength ranges of light). Each emission spectrum, then, may be assigned a value corresponding to that nucleotide. Based upon this analysis, and tracking the cyclical values determined for each site, individual nucleotides and their orders may be determined for each site. These sequences may then be further processed to assemble longer segments including genes, chromosomes, and so forth. As used in this disclosure the terms "automated" and "semi-automated" mean that the operations are performed by system programming or configuration with little or no human interaction once the operations are initiated, or once processes including the operations are initiated.

In the illustrated implementation, reagents 30 are drawn or aspirated into the flow cell through valving 32. The valving may access the reagents from recipients or vessels in which they are stored, such as through pipettes or sippers (not shown in FIG. 1). The valving 32 may allow for selection of the reagents based upon a prescribed sequence of operations performed. The valving may further receive commands for directing the reagents through flow paths 34 into the flow cell 20. Exit or effluent flow paths 36 direct the used reagents from the flow cell 20. In the illustrated implementation, a pump 38 serves to move the reagents through the system 10. The pump 38 may also serve other useful functions, such as measuring reagents or other fluids through the system 10, aspirating air or other fluids, and so forth. Additional valving 40 downstream of pump 38 allows for appropriately directing the used reagent to disposal vessels or recipients 42.

The instrument 12 further includes a range of circuitry that aids in commanding the operation of the various system components, monitoring their operation by feedback from sensors, collecting image data, and at least partially processing the image data. In the implementation illustrated in FIG. 1, a control/supervisory system 44 includes a control system 46 and a data acquisition and analysis system 48. Both systems will include one or more processors (e.g., digital processing circuits, such as microprocessors, multi-core processors, FPGA's, or any other suitable processing circuitry) and associated memory circuitry 50 (e.g., solid state memory devices, dynamic memory devices, on and/or off-board memory devices, and so forth) that may store machine-executable instructions for controlling, for example, one or more computers, processors, or other similar logical devices to provide certain functionality. Application-specific or general purpose computers may at least partially make up the control system and the data acquisition and analysis system. The control system may include, for example, circuitry configured (e.g., programmed) to process commands for fluidics, optics, stage control, and any other useful functions of the instrument. The data acquisition and analysis system 48 interfaces with the optical detection system 26 to command movement of the optical detection system 26 or the stage 22, or both, the emission of light for cyclic detection, receiving and processing of returned signals, and so forth. The instrument may also include various interfaces as indicated at reference 52, such as an operator interface that permits control and monitoring of the instrument 12, loading of samples, launching of automated or semi-automated sequencing operations, generation of reports, and so forth. Finally, in the implementation of FIG. 1, external networks or systems 54 maybe coupled to and cooperate with the instrument 12, for example, for analysis, control, monitoring, servicing, and other operations.

It may be noted that while a single flow cell and fluidics path, and a single optical detection system are illustrated in FIG. 1, in some instruments 12 more than one flow cell and fluidics path may be accommodated. For example, in a presently contemplated implementation, two such arrangements are provided to enhance sequencing and throughput. In practice, any number of flow cells and paths may be provided. These may make use of the same or different reagent receptacles, disposal receptacles, control systems, image analysis systems, and so forth. Where provided, the multiple fluidics systems may be individually controlled or controlled in a coordinated fashion. It is to be understood that the phrase "fluidically connected" may be used herein to describe connections between two or more components that place such components in fluidic communication with one another, much in the same manner that "electrically connected" may be used to describe an electrical connection between two or more components. The phrase "fluidically interposed" may be used, for example, to describe a particular ordering of components. For example, if component B is fluidically interposed between components A and C, then fluid flowing from component A to component C would flow through component B before reaching component C.

Figure 2:
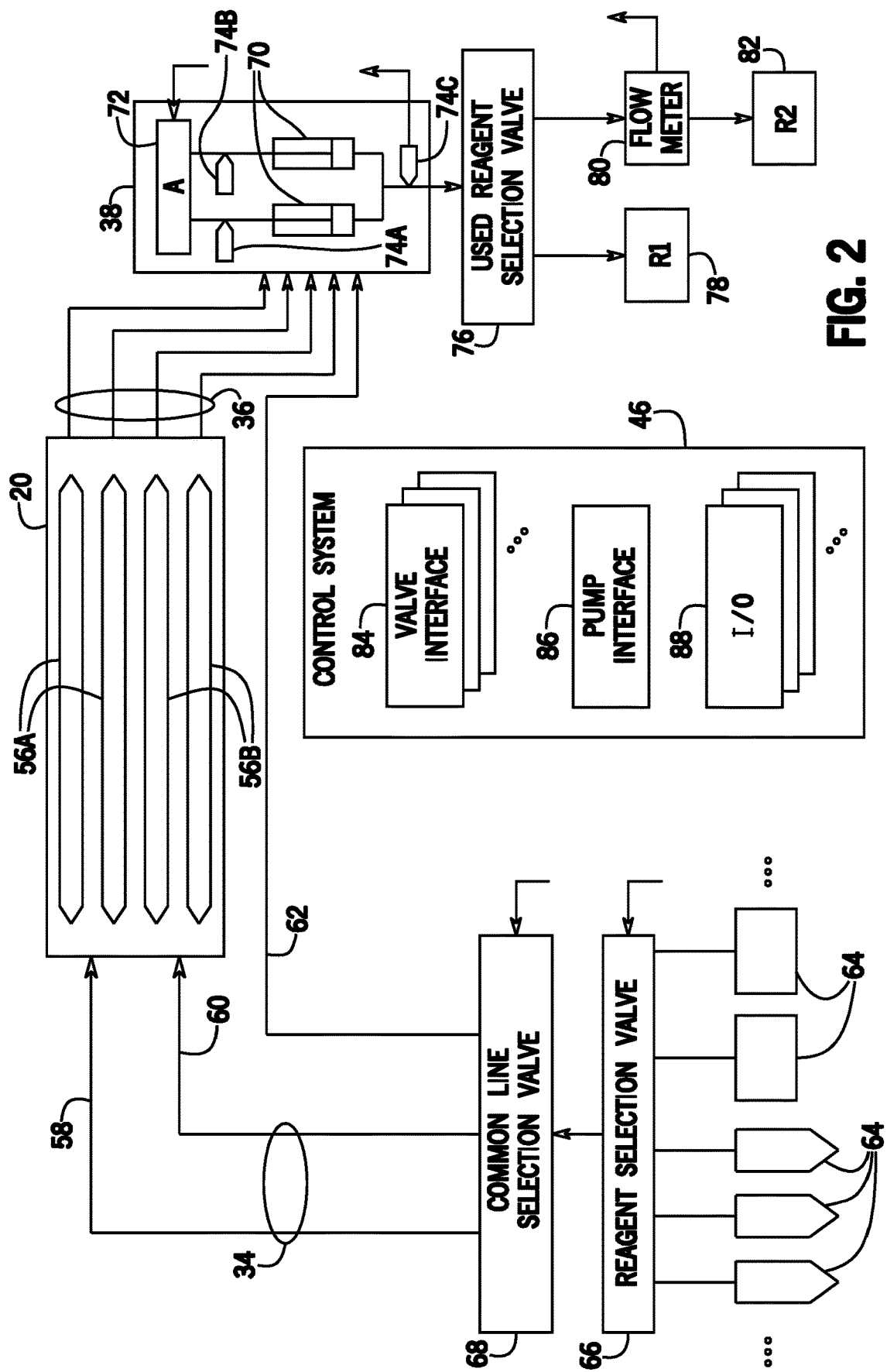
FIG. 2 is a diagrammatical overview of an example fluidic system of the sequencing system of FIG. 1.

FIG. 2 illustrates an example fluidic system of the sequencing system of FIG. 1. In the implementation illustrated, the flow cell 20 includes a series of pathways or lanes 56A and 56B, which may be grouped in pairs for receiving fluid substances (e.g., reagents, buffers, reaction media) during sequencing operations. The lanes 56A are coupled to a common line 58 (a first common line), while the lanes 56B are coupled to a second common line 60. A bypass line 62 is also provided to allow fluids to bypass the flow cell 20 without entering it. As noted above, a series of vessels or recipients 64 allow for the storage of reagents and other fluids that may be utilized during the sequencing operation. A reagent selector valve 66 is mechanically coupled to a motor or actuator (not shown) to allow selection of one or more of the reagents to be introduced into the flow cell. Selected reagents are then advanced to a common line selector valve 68, which similarly includes a motor (not shown). The common line selector valve 68 may be commanded to select one or more of the common lines 58 and 60, or both common lines, to cause the reagents 64 to flow to the lanes 56A and/or 56B in a controlled fashion, or the bypass line 62 to flow one or more of the reagents through the bypass line.

Used reagents exit the flow cell through output lines 36 coupled between the flow cell and the pump 38. In the illustrated implementation, the pump 38 includes a syringe pump having a pair of syringes 70 that are controlled and moved by actuators 72 to aspirate the reagents and other fluids and to expel the reagents and fluids during different operations of the testing, verification and sequencing cycles. The pump assembly may include various other parts and components, including valving, instrumentation, actuators, and so forth (not shown). In the illustrated implementation, pressure sensors 74A and 74B sense pressure on the inlet lines of the pump, while pressure sensor 74C is provided to sense pressures output by the syringe pump.

Fluids used by the system enter a used reagent selector valve 76 from the pump. This valve 76 allows for selection of one of multiple flow paths for used reagents and other fluids. In the illustrated implementation, a first flow path leads to a first used reagent receptacle 78, while a second flow path leads through a flow meter 80 a second used reagent receptacle 82. Depending upon the reagents used, it may be advantageous to collect the reagents, or certain of the reagents in separate vessels for disposal, and the used reagent selector valve 76 allows for such control.

It should be noted that valving within the pump assembly may allow for various fluids, including reagents, solvents, cleaners, air, and so forth to be aspirated by the pump and injected or circulated through one or more of the common lines, the bypass line, and the flow cell. Moreover, as noted above, in a presently contemplated implementation, two parallel implementations of the fluidics system shown in FIG. 2 are provided under common control. Each of the fluidics systems may be part of a single sequencing instrument, and may carry out functions including sequencing operations on different flow cells and sample libraries in parallel.

The fluidics system operates under the command of control system 46 which implements prescribed protocols for testing, verification, sequencing, and so forth. The prescribed protocols will be established in advance and include a series of events or operations for activities such as aspirating reagents, aspirating air, aspirating other fluids, expelling such reagents, air and fluids, and so forth. The protocols will allow for coordination of such fluidic operations with other operations of the instrument, such as reactions occurring in the flow cell, imaging of the flow cell and its sites, and so forth. In the illustrated implementation, the control system 46 employs one or more valve interfaces 84 which are configured to provide command signals for the valves, as well as a pump interface 86 configured to command operation of the pump actuator 72. Various input/output circuits 88 may also be provided for receiving feedback and processing such feedback, such as from the pressure sensors 74A-C and flow meter 80.

Figure 3:
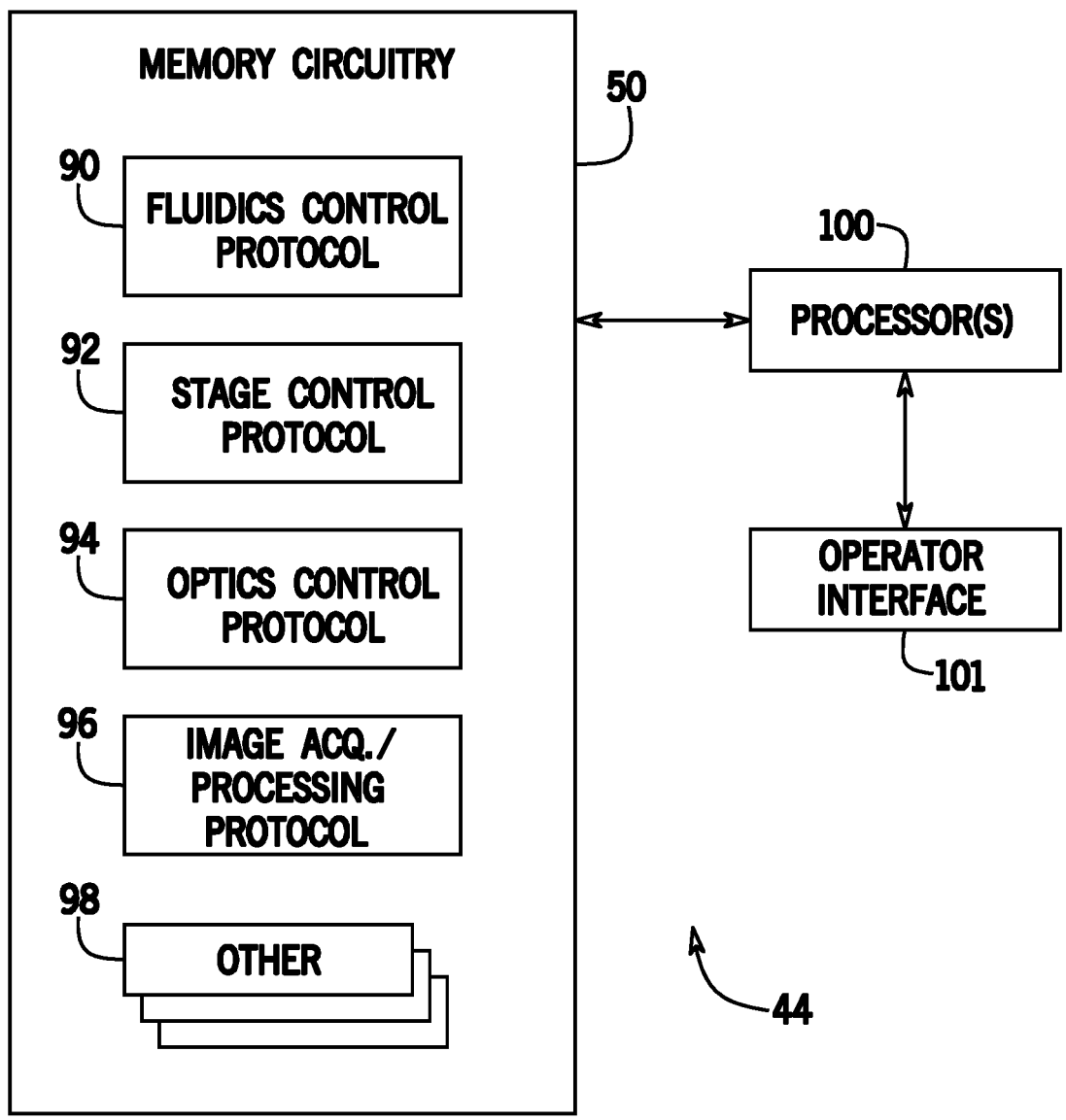
FIG. 3 is a diagrammatical overview of an example processing and control system of the sequencing system of FIG. 1.

FIG. 3 illustrates certain functional components of the control/supervisory system 44. As illustrated, the memory circuitry 50 stores prescribed routines that are executed during testing, commissioning, troubleshooting, servicing, and sequencing operations. Many such protocols and routines may be implemented and stored in the memory circuitry, and these may be updated or altered from time to time. As illustrated in FIG. 3, these may include a fluidics control protocol 90 for controlling the various valves, pumps, and any other fluidics actuators, as well as for receiving and processing feedback from fluidics sensors, such as valves, and flow and pressure sensors. A stage control protocol 92 allows for moving the flow cell as desired, such as during imaging. An optics control protocol 94 allows for commands to be issued to the imaging components to illuminate portions of the flow cell and to receive returned signals for processing. An image acquisition and processing protocol 96 allows for the image data to be at least partially processed for extraction of useful data for sequencing. Other protocols and routines may be provided in the same or different memory circuitry as indicated by reference 98. In practice, the memory circuitry may be provided as one or more memory devices, such as both volatile and non-volatile memory. These memories may be within the instrument and/or off-board.

One or more processors 100 access the stored protocols and implement them on the instrument. As noted above, the processing circuitry may be part of application-specific computers, general-purpose computers, or any suitable hardware, firmware and software platform. The processors and the operation of the instrument may be commanded by human operators via an operator interface 101. The operator interface may allow for testing, commissioning, troubleshooting, and servicing, as well as for reporting any issues that may arise in the instrument. The operator interface may also allow for launching and monitoring sequencing operations.

Returning to FIG. 2, the syringes 70 of the pump 38 may aspirate used reagents from the flow cell 20 via the output lines 36. The used reagent selector valve 76 may receive the used reagents and route the used reagents to one of multiple used reagent receptacles 78, 82. Though two used reagent receptacles 78, 82 are shown in FIG. 2, implementations having more than two used reagent receptacles 78, 82 are also envisaged. Because the various reagents used by the instrument may have different disposal procedures, using the used reagent valve 76 to separate used reagents into various used reagent receptacles 78, 82 may allow for disposal of the various used reagents in different ways.

For example, based on a known sequencing protocol, the control system 46 may know that a first used reagent will be pumped out of the flow cell 20 next (e.g., the reagent selected by the reagent selector valve 66). The control system 46, via the valve interface 84, may actuate the used reagent selector valve 76 to a first position, such that the used reagent selector valve 76 receives the first used reagent and routes the first used reagent to the first used reagent receptacle 78 via the first disposal path. As the sequencing operation proceeds according to the sequencing protocol, a second reagent may be pumped through the flow cell 20. The control system 46, via the valve interface, may actuate the used reagent selector valve 76 to a second position, such that the used reagent selector valve 76 receives the second used reagent and routes the second used reagent to the second used reagent receptacle 82 via the second disposal path.

The second disposal path may include a flow meter 80 to detect the flow of reagent through the second disposal path. It should be understood, however, that in some implementations, the flow meter may detect flow of reagent through the first disposal path, rather than the second disposal path. The flow meter 80 communicates with the control system 46 via the input/output circuits 88, such that the control system 46 may consider outputs from the flow meter 80 in determining the position of the used reagent selector valve 76. In some implementations, the flow meter 80 may be placed upstream of the used reagent selector valve 76, but this may prevent such implementations from being able to detect if liquids are flowing through the correct disposal path. In some other or additional implementations, flow meters may be installed at each disposal path downstream of the user reagent selector valve 76 and may be used to directly measure the flow rate through each disposal path, although this may require additional flow meters and expense.

For example, if the used reagent selector valve 76 is assumed to be or indicated as being in the first position to select the first disposal path to the first used reagent receptacle 78, but the flow meter 80 indicates that fluid is flowing through the second disposal path, the control system 46 may cease operations and notify the operator. On the other hand, if the used reagent selector valve 76 is in the first position to select the first disposal path to the first used reagent receptacle 78 and the flow meter 80 indicates that fluid is not flowing through the second disposal path, then sequencing operations may continue since the fluid appears to be flowing correctly (or at least not down an incorrect flow path). Correspondingly, if the used reagent selector valve 76 is in the second position to select the second disposal path to the second used reagent receptacle 82 and the flow meter 80 indicates that fluid is flowing through the second disposal path, then sequencing operations may continue. However, if the used reagent selector valve 76 is in the second position to select the second disposal path to the second used reagent receptacle 82, but the flow meter 80 indicates that fluid is not flowing through the second disposal path, the control system 46 may cease operations and notify the operator.

The system 10 may use significantly more of one reagent than another. For example, the first reagent may account for about 1%, 2%, 3%, 4%, 5%, 8%, 10%, 15%, 20%, 30%, 40%, 50%, 60%, 70%, 80%, 85%, 90%, 92%, 95%, 96%, 97%, 98%, 99%, or any other value of the total effluent volume, wherein the term "about" indicates 10% or less variance from the stated values. For example, the system may use more of the second reagent than the first reagent. In such an implementation, the flow meter 80 may be coupled to the disposal path corresponding to the more-used reagent. The second used reagent receptacle 82 may be substantially larger than the first used reagent receptacle 78, accommodating a larger volume of fluid. In other implementations, the receptacles 78, 82 may be the same or similar sizes, but emptied on different schedules.

Figure 4:
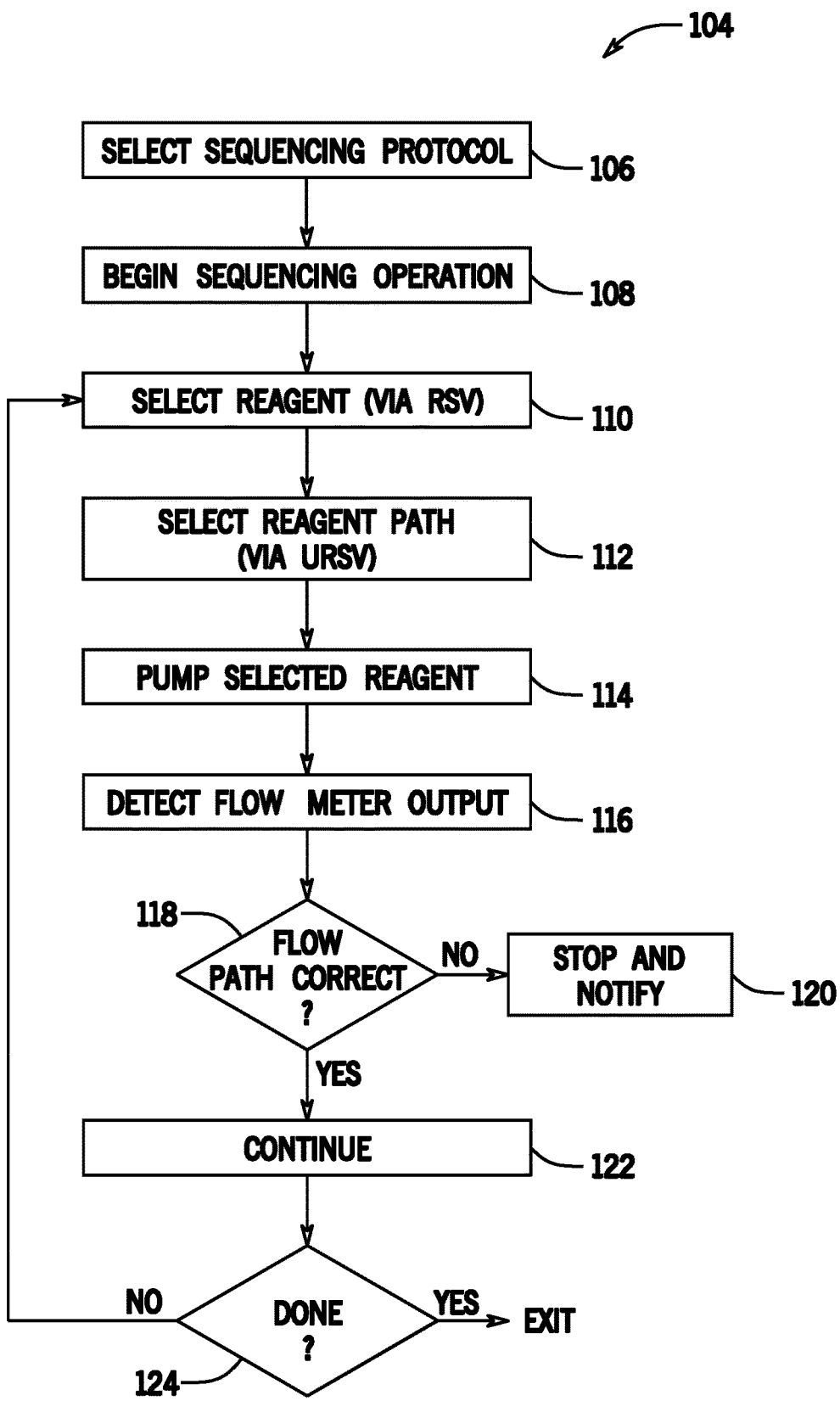
FIG. 4 is a flow chart of an example process for operating the sequencing system of FIG. 1 during a sequencing operation.

FIG. 4 is a flow chart of a process 104 for operating the instrument 12 shown in FIG. 1 during an analysis operation (e.g., a sequencing operation). At 106, a sequencing protocol may be selected. As discussed above, the sequencing protocol may be selected by an operator via the interface shown in FIG. 1, or remotely via the external networks/systems. In other implementations, the sequencing protocol may be selected automatically based on a pre-programmed schedule.

The sequencing operation may begin at 108 based on the selected sequencing protocol. The control system controls the instrument in its performance of the sequencing operation. At 110, the reagent selector valve, under the control of the control system, may select a particular reagent or set of reagents (in some implementations, multiple reagents and or other substances may be pre-mixed or mixed before being routed through the flow cell—reference to "the reagent," the "selected reagent," and so forth below is to be understood to be inclusive of both single reagents and combinations of reagents). This selection may be based on the selected sequencing protocol. At 112, the common line selector valve and the used reagent selector valve, under the control of the control system, may select a reagent flow path through the flow cell (or bypass line) and a downstream disposal flow path, respectively. As discussed above, the common line selector valve may route the selected reagent to the A lanes of the flow cell via the first common line, to the B lanes of the flow cell via the second common line, to both the A and B lanes of the flow cell via the first and second common lines, respectively, or the common line selector valve may route the selected reagent to the bypass line to bypass the flow cell. Similarly, based on the selected reagent, the used reagent selector valve may select a disposal path such that the used reagent flows to the used reagent receptacle corresponding to the selected reagent. The used reagent selector valve may be actuated such that used reagent received from the effluent line(s) leading to the used reagent selector valve flows along the selected disposal path to the corresponding used reagent receptacle.

At 114, a reagent is pumped through the reagent selector valve, the common line selector valve, and the common lines and through the flow cell (or, alternatively, through the bypass line). As discussed above, the reagents are pumped by the pump. For example, an actuator may move the plungers of syringes to draw reagents through the flow cell or the bypass line into the syringes. The actuator may then move the plungers of the syringes in the opposite direction to expel used reagent via the effluent line(s) to the used reagent selector valve. Used reagent flows from the selected reagent path through the used reagent selector valve and to one of the used reagent receptacles via one of the disposal paths.

At 116, the flow meter may detect the rate of fluid flow along the second disposal path to the second used reagent receptacle and may provide a signal indicative of the flow rate to the control system. At 118, the control system may determine whether used reagent is flowing along the selected disposal path. The fluid flow rate through the second disposal path may help the control system to determine whether or not the used reagent selector valve is in the selected position, as discussed earlier. If the used reagent is not flowing along the selected disposal path, or if the used reagent is flowing along a disposal path that is not selected, the control system may stop operations and notify the operator (at 120). At 122, if the used reagent is flowing along the selected disposal path, or if the used reagent is not flowing along a disposal path that is not selected, the control system may assume that the used reagent selector valve is in the correct position and continue the sequencing operation.

For example, if the first disposal path is selected (i.e., used reagent flows through the used reagent selector valve along the first disposal path and to the first used reagent receptacle), but the flow meter indicates that fluid is flowing through the second disposal path, the control system may cease operations and notify the operator. On the other hand, if the first disposal path is selected (i.e., used reagent flows through the used reagent selector valve along the first disposal path and to the first used reagent receptacle), and the flow meter indicates that fluid is not flowing through the second disposal path, then sequencing operation will continue. Correspondingly, if the second disposal path is selected (i.e., used reagent flows through the used reagent selector valve along the second disposal path and to the second used reagent receptacle), and the flow meter indicates that fluid is flowing through the second disposal path, then sequencing operation will continue. However, if the second disposal path is selected (i.e., used reagent flows through the used reagent selector valve along the second disposal path and to the second used reagent receptacle), but the flow meter indicates that fluid is not flowing through the second disposal path, the control system may cease operations and notify the operator.

At 124, the control system may determine whether the sequencing operation is complete. If the sequencing operation is complete, the system may exit the process 104. If the sequencing operation is not complete, the process 104 may return to 110 to select another reagent (or reagents).

Figure 5A:
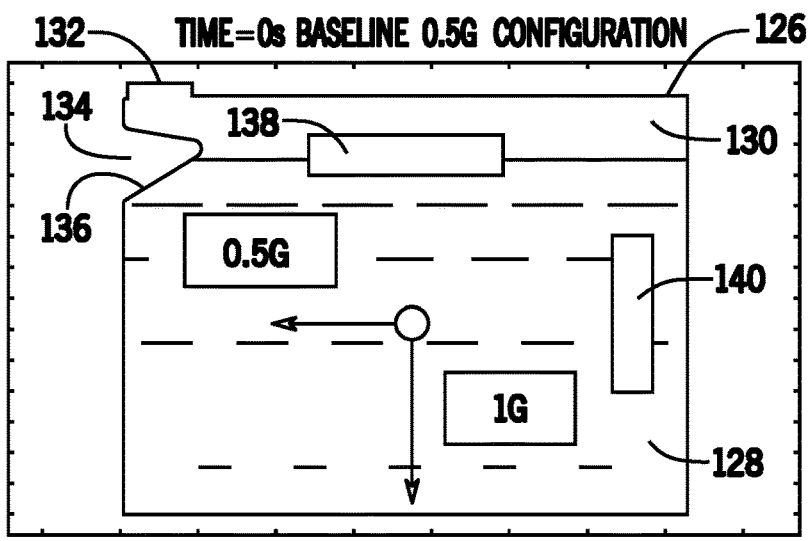
FIG. 5A illustrates, in one example, liquid slosh in a used reagent vessel experiencing a 0.5 G side load, simulating removal or transport of the vessel at a time of 0.0 seconds.
Figure 5B:
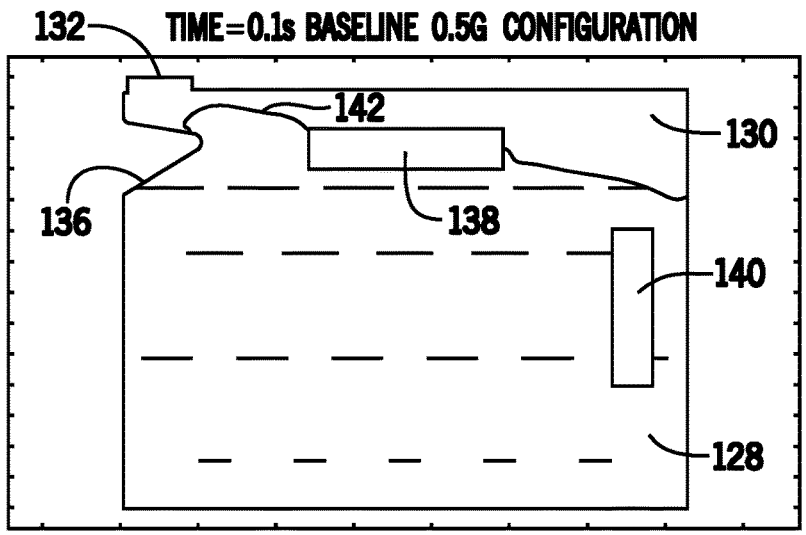
FIG. 5B illustrates, in one example, the used reagent vessel of FIG. 5A at a time of 0.1 seconds after the side load of 0.5 G has been applied.
Figure 5C:
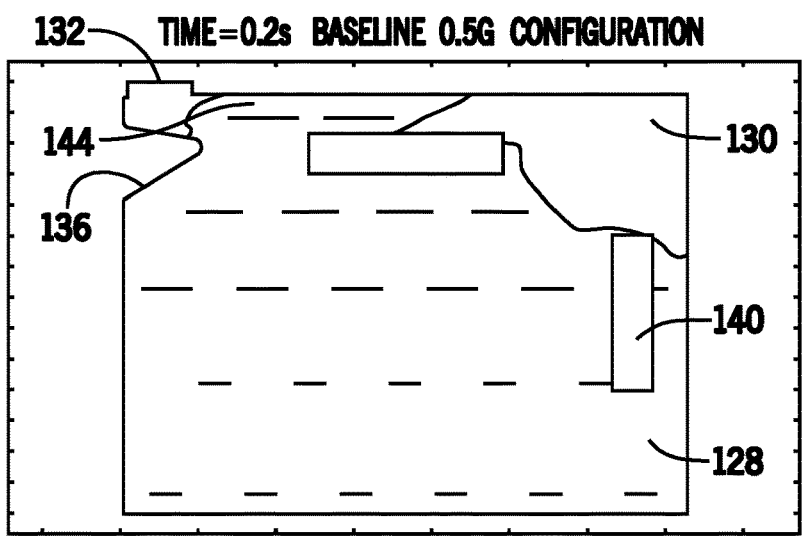
FIG. 5C illustrates, in one example, the used reagent vessel of FIG. 5A at a time of 0.2 seconds after the side load of 0.5 G has been applied.

FIGS. 5A-5C illustrate liquid slosh in a used reagent vessel 126 experiencing a 0.5 G side load simulating removal or transport of the vessel 126. It should be understood, however, that 0.5 G is merely an example of typical loads on the vessel 126 during installation, removal, and transport. Accordingly, in application the vessel 126 may withstand loads less than and/or greater than 0.5 G. FIG. 5A shows the vessel 126 at a time of 0.0 seconds. As illustrated, the vessel 126 is partially filled with used reagent 128. The remaining volume of the vessel 126 is filled with ambient air 130. The vessel 126 includes an opening 132 through which used reagent 128 enters and exits the vessel 126. The vessel 126 also includes a recess 134 defined on one side by a redirecting surface 136 to prevent sloshing used reagent 128 from exiting the vessel 126 via the opening 132. A top handle 138 and a side handle 140 aid in removal and transport of the vessel 126.

FIG. 5B shows the vessel 126 at a time of 0.1 seconds after a side load of 0.5 G has been applied. As shown, a wave 142 forms in the used reagent 128 and propagates toward the opening 132. However, once the wave 142 reaches the redirecting surface 136, the redirecting surface 136 redirects the wave 142 away from the opening 132 such that the used reagent 128 does not exit the opening 132.

FIG. 5C shows the vessel 126 at a time of 0.2 seconds after a side load of 0.5 G has been applied. As shown, the wave 142 has been redirected by the redirecting surface 136, forming a secondary wave 144, which propagates back across the vessel 126, in a direction opposite the first wave 142. Accordingly, the vessel may withstand substantial fluid slosh during removal or transport of the vessel 126 (e.g., to dispose of use reagent 128) without used reagent 128 exiting the opening 132 of the vessel 126. As previously described, it should be understood that the 0.5 G side load described is merely an example of typical handling conditions. Accordingly, the vessel 126 may be capable with withstanding substantially more than 0.5 G without used reagent 128 exiting the opening 132.

The sequencing system may flow multiple reagents through one or more flow cells in the performance of a sequencing operation. The various reagents may have different characteristics from one another such that disposal procedures may differ from reagent to reagent. Accordingly, the instrument includes a used reagent selector valve configured to route a used reagent to an appropriate used reagent receptacle based on the reagent being pumped through the flow cell at the time, according to a sequencing protocol, such that the various used reagents may be disposed of in different ways.

In addition to being used to detect whether liquids are flowing through the correct disposal path, the flow meter may also be used to determine if there is leakage in the fluidic system. For example, a syringe pump may be actuated so as to draw a pre-defined amount of liquids from one or more reagent recipients, through the flow cell, and into the syringe; the syringe pump may then be actuated so as to expel those liquids through the metered disposal path. If the amount of liquid that is measured by the flow meter is outside of a permissible threshold amount from the pre-defined amount, then an error notification may be generated to alert the user as to a potential leak or other fault.

It is also to be understood that the various techniques discussed above may be implemented in a diagnostic mode outside of normal analysis/processing operations. For example, after installation of a flow cell cartridge and/or reagent cartridges in an analysis system, one or more of the fluidic flow paths (or all of them) leading through or to the flow cell cartridge and/or reagent cartridges may be tested using the flow meter, as discussed above. For example, predefined amounts of reagents associated with each fluidic flow path may be pumped through the fluidic system and through the flow meter in order to measure how much of each reagent is actually delivered to the metered disposal paths; if the metered amount of fluid that passes through the flow meter is outside of a threshold amount, e.g., ±10% of the predetermined amount, then the flow path may be determined to be defective, and a notification may be produced to alert the user. Similarly, different disposal paths may be selected during such test flows, and the flow meter may be used to determine if fluid flow is detected in a non-selected disposal path, as discussed earlier herein. If so, then a notification may be produced to alert the user. If the diagnostic mode is completed without any errors or warnings, then the apparatus may proceed to be used for routine analysis. In some such implementations, there may be no further flow meter measurements, although in other implementations, flow meter measurements may continue and may be used to determine, for example, if there are potential leaks or failures in disposal path selection.

The use, if any, of ordinal indicators, e.g., (a), (b), (c) . . . or the like, in this disclosure and claims is to be understood as not conveying any particular order or sequence, except to the extent that such an order or sequence is explicitly indicated. For example, if there are three steps labeled (i), (ii), and (iii), it is to be understood that these steps may be performed in any order (or even concurrently, if not otherwise contraindicated) unless indicated otherwise. For example, if step (ii) involves the handling of an element that is created in step (i), then step (ii) may be viewed as happening at some point after step (i). Similarly, if step (i) involves the handling of an element that is created in step (ii), the reverse is to be understood.

It is also to be understood that the use of "to," e.g., "a valve to switch between two flow paths," may be replaceable with language such as "configured to," e.g., "a valve configured to switch between two flow paths", or the like.

Terms such as "about," "approximately," "substantially," "nominal," or the like, when used in reference to quantities or similar quantifiable properties, are to be understood to be inclusive of values within ±10% of the values specified, unless otherwise indicated.

In addition to the claims listed in this disclosure, the following additional implementations are to be understood to be within the scope of this disclosure:

Implementation 1: A system including: a flow cell through which a plurality of reagents is pumped during a genetic sequencing operation; an effluent line that, in operation, conducts a used reagent; a used reagent valve configured to receive the used reagent from the effluent line and controllable to select one of a plurality of disposal paths for the used reagent; and control circuitry coupled to the used reagent valve that, in operation, controls the used reagent valve to select a desired one of the disposal paths depending upon which reagent is being pumped though the flow cell.

Implementation 2: The system of implementation 1, including a flow meter that, in operation, is to detect flow of reagent and provide flow data to the control circuitry.

Implementation 3: The system of implementation 2, in which the flow meter is coupled to one of the disposal paths, and in which the control circuitry is to determine whether the desired flow path is properly selected based upon feedback from the flow meter.

Implementation 5: The system of implementation 3, in which a first of the disposal paths conveys more used reagent than a second of the disposal paths during the sequencing operation, and in which the flow meter is coupled to the first disposal path.

Implementation 6: The system of implementation 1, in which the control circuitry is to control the used reagent valve based upon a prescribed sequencing protocol for a genetic sequencer.

Implementation 7: The system of implementation 6, including at least one valve to select a reagent and a reagent flow path, and in which the control circuitry is to control the at least one valve and the used reagent valve based upon the prescribed sequencing protocol.

Implementation 8: The system of implementation 7, including a reagent pump disposed between the reagent flow path and the effluent line.

Implementation 9: The system of implementation 1, including a first used reagent vessel to receive effluent from a first disposal path and a second reagent vessel to receive effluent from a second disposal path.

Implementation 10: The system of implementation 1, in which the first used reagent vessel is to direct fluid therein to be directed away from an opening of the first used reagent vessel when the fluid is moved during removal or transport of the first used reagent vessel.

Implementation 11: A system including: a flow cell through which a plurality of reagents is pumped during a genetic sequencing operation; at least one reagent valve to select a reagent and a reagent flow path, at least one of the reagent flow paths passing through the flow cell; an effluent line that, in operation, is to conduct used reagent; a used reagent valve configured to receive used reagent from the effluent line and to controllable to select one of a plurality of disposal paths for the used reagent; and control circuitry coupled to the at least one reagent valve and to the used reagent valve, the control circuitry, in operation, is to control the at least one reagent valve and the used reagent valve based upon a prescribed sequencing protocol for the genetic sequencing operation.

Implementation 12: The system of implementation 11, in which the control circuitry, in operation, is to select a desired one of the disposal paths depending upon which reagent is being pumped though the flow cell.

Implementation 13: The system of implementation 11, including a flow meter that, in operation, is to detect flow of reagent and provides flow data to the control circuitry.

Implementation 14: The system of implementation 13, in which the flow meter is coupled to one of the disposal paths, and in which the control circuitry determines whether the desired flow path is properly selected based upon feedback from the flow meter.

Implementation 15: The system of implementation 14, in which a first of the disposal paths conveys more used reagent than a second of the disposal paths during the sequencing operation, and in which the flow meter is coupled to the first disposal path.

Implementation 16: A method including: performing a genetic sequencing operation by pumping a plurality of reagents through a flow cell; during the genetic sequencing operation, controlling at least one reagent valve to select desired reagents to be pumped thought the flow cell in accordance with a protocol for the genetic sequencing operation; and controlling a used reagent valve, during the genetic sequencing operation, to select one of a plurality of disposal paths for used reagent after being pumped through the flow cell based upon the protocol for the genetic sequencing operation.

Implementation 17: The method of implementation 16, including detecting flow through at least one of the disposal paths to verify that a desired disposal path is properly selected based upon the protocol for the genetic sequencing operation.

Implementation 18: The method of implementation 17, in which the flow is detected by a flow meter coupled to one of the disposal paths, and in which the control circuitry is to determine whether the desired flow path is properly selected based upon feedback from the flow meter.

Implementation 19: The method of implementation 18, in which a first of the disposal paths are to convey more used reagent than a second of the disposal paths during the sequencing operation, and in which the flow meter is coupled to the first disposal path.

Implementation 20: The method of implementation 16, including collecting the used reagent in at least two different vessels based upon which disposal path is selected.

It should be appreciated that all combinations of the foregoing concepts (provided such concepts are not mutually inconsistent) are contemplated as being part of the inventive subject matter disclosed herein. All combinations of the claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

What is claimed is:
1. A system comprising:
one or more effluent flow paths to fluidically connect with a flow cell through which a plurality of reagents is to be pumped during a genetic sequencing operation, wherein the one or more effluent paths are to receive used reagents from the flow cell;
one or more pumps to pump the used reagents through the one or more effluent flow paths;

a used reagent selector valve to receive used reagents from the one or more pumps via an effluent line and controllable to select one of a plurality of disposal paths for the used reagents;
control circuitry operatively coupled to the used reagent selector valve, the control circuitry having one or more processors and a memory to store machine-executable instructions which, upon being executed by the one or more processors, control the one or more processors to cause the used reagent selector valve to select a desired one of the disposal paths depending upon which used reagent is being pumped through the one or more effluent paths; and
a flow meter that, in operation, is to detect a flow state of used reagents and provide flow data to the control circuitry regarding the flow of the used reagents, wherein the flow meter is fluidically coupled to one of the disposal paths, wherein the memory is to store further machine-executable instructions which, upon being executed by the one or more processors, further control the one or more processors to determine that the used reagent is not flowing through the desired disposal path based on the detected flow state and to provide a notification based on the determination that the used reagent is not flowing through the desired disposal path.

2. The system of claim 1, wherein a first disposal path of the disposal paths conveys more used reagent than a second disposal path of the disposal paths during the sequencing operation and wherein the flow meter is coupled to the first disposal path.

3. The system of claim 1, wherein the memory is to store further machine-executable instructions which, upon being executed by the one or more processors, further control the one or more processors to control the used reagent selector valve based upon a prescribed sequencing protocol for a genetic sequencer.

4. The system of claim 3, further comprising at least one valve to select a reagent and a reagent flow path, and wherein the memory is to store further machine-executable instructions which, upon being executed by the one or more processors, further control the one or more processors to control the at least one valve and the used reagent selector valve based upon the prescribed sequencing protocol.

5. The system of claim 4, wherein the one or more pumps include a reagent pump fluidically interposed between the reagent flow path and the effluent line.

6. The system of claim 1, further comprising a first used reagent vessel to receive used reagent from a first disposal path of the disposal paths and a second used reagent vessel to receive used reagent from a second disposal path of the disposal paths.

7. The system of claim 1, wherein a first used reagent vessel is to direct fluid therein to be directed away from an opening of the first used reagent vessel when the fluid is moved during removal or transport of the first used reagent vessel.

8. A system comprising:
a flow cell through which a plurality of reagents is pumped during a genetic sequencing operation to produce used reagents;
at least one reagent selector valve to select a reagent and a reagent flow path from a plurality of reagent flow paths, at least one of the reagent flow paths passing through the flow cell;
an effluent line that, in operation, is to conduct used reagent;
a used reagent selector valve to receive used reagent from the effluent line and controllable to select one of a plurality of disposal paths for the used reagent;
control circuitry operatively coupled to the at least one reagent selector valve and to the used reagent selector valve, the control circuitry having one or more processors and a memory to store machine-executable instructions which, upon being executed by the one or more processors, control the one or more processors to control the at least one reagent selector valve and the used reagent selector valve based upon a prescribed sequencing protocol for the genetic sequencing operation; and
a flow meter that, in operation, is to detect a flow state of the reagents and provide flow data to the control circuitry, wherein the flow meter is coupled to one of the disposal paths, wherein the memory is to store further machine-executable instructions which, upon being executed by the one or more processors, further control the one or more processors to determine that the reagents are not flowing through the selected disposal path based on the detected flow state and to provide a notification based on the determination that the used reagent is not flowing through the selected disposal path.

9. The system of claim 8, wherein the memory is to store further machine-executable instructions which, upon being executed by the one or more processors, further control the one or more processors to select a desired one of the disposal paths depending upon which reagent is being pumped though the flow cell.

10. The system of claim 8, wherein a first disposal path of the disposal paths conveys more used reagent than a second disposal path of the disposal paths during the sequencing operation, and wherein the flow meter is fluidically coupled to the first disposal path.

11. A method comprising:
performing a genetic sequencing operation by pumping, with one or more pumps, a plurality of reagents through a flow cell to produce used reagents, wherein there are one or more effluent paths that fluidically connect with the flow cell, wherein the one or more effluent paths receive the used reagents from the flow cell;
during the genetic sequencing operation, controlling, with control circuitry having one or more processors and a memory, at least one reagent selector valve to select desired reagents to be pumped through the flow cell in accordance with a protocol for the genetic sequencing operation;
during the genetic sequencing operation, controlling, with the control circuitry, a used reagent selector valve to select one of a plurality of disposal paths for the used reagents after the used reagents exit the flow cell via an effluent line, the controlling of the used reagent selector valve using the protocol for the genetic sequencing operation;
detecting a flow state through at least one of the disposal paths to verify that used reagents are flowing through the selected disposal path, wherein the flow state is detected by a flow meter fluidically coupled to one of the disposal paths;
determining that the used reagents are not flowing through the selected disposal path based on the detected flow state; and
providing a notification based on the determination that the used reagents are not flowing through the selected disposal path.

12. The method of claim 11, wherein a first disposal path of the disposal paths conveys more used reagent than a second disposal path of the disposal paths during the sequencing operation, and wherein the flow meter is fluidically coupled to the first disposal path.

13. The method of claim 11, further comprising collecting the used reagents in at least two different vessels, each disposal vessel positioned to receive used reagents from a different disposal path.

14. The method of claim 11, wherein the flow meter is fluidically coupled to a given one of the disposal paths other than the selected disposal path and wherein the flow state comprises flow through the given one of the disposal paths.

15. The method of claim 11, wherein the flow meter is fluidically coupled to the selected disposal path and wherein the flow state comprises no flow through the selected disposal path.

16. The system of claim 1, wherein the flow meter is fluidically coupled to a given one of the disposal paths other than the desired disposal path and wherein the flow state comprises flow through the given one of the disposal paths.

17. The system of claim 1, wherein the flow meter is fluidically coupled to the desired disposal path and wherein the flow state comprises no flow through the desired disposal path.

18. The system of claim 8, wherein the flow meter is fluidically coupled to a given one of the disposal paths other than the selected disposal path and wherein the flow state comprises flow through the given one of the disposal paths.

19. The system of claim 8, wherein the flow meter is fluidically coupled to the selected disposal path and wherein the flow state comprises no flow through the selected disposal path.

* * * * *